US012350054B2

(12) United States Patent
Yu et al.

(10) Patent No.: US 12,350,054 B2
(45) Date of Patent: Jul. 8, 2025

(54) STRETCHABLE AND WEARABLE WIRELESS 3-LEADS ECG MONITORING APPARATUS

(71) Applicant: City University of Hong Kong, Hong Kong (HK)

(72) Inventors: Xinge Yu, Hong Kong (HK); Yiming Liu, Hong Kong (HK); Jingkun Zhou, Hong Kong (HK)

(73) Assignee: City University of Hong Kong, Hong Kong (HK)

( * ) Notice: Subject to any disclaimer, the term of this patent is extended or adjusted under 35 U.S.C. 154(b) by 354 days.

(21) Appl. No.: 17/838,251

(22) Filed: Jun. 12, 2022

(65) Prior Publication Data
US 2023/0021804 A1  Jan. 26, 2023

Related U.S. Application Data

(60) Provisional application No. 63/214,308, filed on Jun. 24, 2021.

(51) Int. Cl.
*A61B 5/271* (2021.01)
*A61B 5/00* (2006.01)
*A61B 5/259* (2021.01)
*A61B 5/308* (2021.01)
(Continued)

(52) U.S. Cl.
CPC ............ *A61B 5/271* (2021.01); *A61B 5/0006* (2013.01); *A61B 5/259* (2021.01); *A61B 5/308* (2021.01); *A61B 5/339* (2021.01); *A61B 5/349* (2021.01); *A61B 5/7203* (2013.01);
(Continued)

(58) Field of Classification Search
None
See application file for complete search history.

(56) References Cited

U.S. PATENT DOCUMENTS

2005/0197586 A1* 9/2005 Pearlman ............. A61B 5/7267
600/509
2010/0262029 A1* 10/2010 Kelly .................... A61B 5/361
600/518
(Continued)

OTHER PUBLICATIONS

Jianchun Song et al., Mechanically and Electronically Robust Transparent Organohydrogel Fibers. Adv. Mater. 2020, 32, 1906994. https://doi.org/10.1002/adma.201906994, viewed on Jun. 29, 2024 (Year: 2020).*

(Continued)

*Primary Examiner* — Catherine M Voorhees
*Assistant Examiner* — James Moss
(74) *Attorney, Agent, or Firm* — Idea Intellectual Limited; Margaret A. Burke; Sam T. Yip

(57) ABSTRACT

The present invention provides a stretchable and flexible multi-leads ECG monitoring apparatus having a primary circuitry encased in a thin and flexible polymer patch configured to be worn on a human body. At least four flexible leads are connected to the primary circuitry at a first end and are configured to be connected to ECG electrode patches at a second end. The ECG electrode patches being configured to be attached to a plurality positions on a human body. The wireless transmitter is configured to transmit the ECG monitoring signals to a receiving device for recording or displaying the ECG monitoring signal.

18 Claims, 11 Drawing Sheets

(51) Int. Cl.
A61B 5/339 (2021.01)
A61B 5/349 (2021.01)
(52) U.S. Cl.
CPC ............ *A61B 5/7455* (2013.01); *A61B 5/746* (2013.01); *A61B 2562/222* (2013.01)

(56) References Cited

U.S. PATENT DOCUMENTS

| | | | | |
|---|---|---|---|---|
| 2012/0226129 | A1* | 9/2012 | Callahan ................ | A61B 5/303 600/509 |
| 2013/0041235 | A1* | 2/2013 | Rogers ................. | H05K 1/0283 600/386 |
| 2013/0099358 | A1* | 4/2013 | Elolampi ............. | H05K 1/0346 257/618 |
| 2014/0340857 | A1* | 11/2014 | Hsu ..................... | H01L 23/5386 174/254 |
| 2016/0099227 | A1* | 4/2016 | Dalal .................. | H01L 23/5389 257/773 |
| 2016/0287177 | A1* | 10/2016 | Huppert ............... | A61B 5/4839 |
| 2016/0338646 | A1* | 11/2016 | Lee ....................... | A61B 5/308 |
| 2017/0095670 | A1* | 4/2017 | Ghaffari ................ | A61M 21/02 |
| 2018/0116513 | A1* | 5/2018 | Bhogu .................. | A61B 5/316 |
| 2020/0037877 | A1* | 2/2020 | Ott ....................... | H04W 56/0015 |
| 2020/0155072 | A1* | 5/2020 | Szumanski .......... | A61B 5/6843 |

OTHER PUBLICATIONS

Zixuan Wu et al., ACS Applied Materials & Interfaces 2021 13 (2), 2128-2144, DOI: 10.1021/acsami.0c21841, https://pubs.acs.org/doi/full/10.1021/acsami.0c21841, viewed on Dec. 20, 2024 (Year: 2021).*

Venkatesan, C., Karthigaikumar, P., Paul, A., Satheeskumaran, S. & Kumar, R. ECG Signal Preprocessing and SVM Classifier-Based Abnormality Detection in Remote Healthcare Applications. IEEE Access, 2018, 6, 9767-9773, doi:10.1109/access.2018.2794346.

Desai, U., Martis, R. J., Nayak, C. G., Sarika, K. & Seshikala, G. "Machine Intelligent Diagnosis of ECG for Arrhythmia Classification Using DWT, ICA and SVM Techniques" in 2015 Annual IEEE India Conference (INDICON). 1-4 (IEEE).

Kumar, R. G. & Kumaraswamy, Y. J. I. J. C. A. ,Investigating cardiac arrhythmia in ECG using random forest classification, International Journal of Computer Applications, vol. 37, issue 4, pp. 31-34.

Salem, M., Taheri, S. & Yuan, J.-S. "ECG Arrhythmia Classification Using Transfer Learning from 2-Dimensional Deep CNN Features" 2018 IEEE Biomedical Circuits and Systems Conference (BioCAS).

Rubin, J., Parvaneh, S., Rahman, A., Conroy, B. & Babaeizadeh, S. J. J. o. e. Densely connected convolutional networks for detection of atrial fibrillation from short single-lead ECG recordings. 2018, 51, S18-S21.

Liu, Y., Zheng, H., Zhao, L. et al. Electronic Skin from High-Throughput Fabrication of Intrinsically Stretchable Lead Zirconate Titanate Elastomer. Research (Wash D C), 2020, 2020, 1085417, doi:10.34133/2020/1085417.

Liu, Y., Huang, X., Zhou, J. et al. Bandage based energy generators activated by sweat in wireless skin electronics for continuous physiological monitoring. Nano Energy, 2022, 92, doi:10.1016/j.nanoen.2021.106755.

Yu, X., Xie, Z., Yu, Y. et al. Skin-integrated wireless haptic interfaces for virtual and augmented reality. Nature, 2019, 575, 473-479.

Song, E., Xie, Z., Bai, W. et al. Miniaturized electromechanical devices for the characterization of the biomechanics of deep tissue. Nat Biomed Eng, 2021, 5, 759-771, doi:10.1038/s41551-021-00723-y.

Li, D., He, J., Song, Z. et al. Miniaturization of mechanical actuators in skin-integrated electronics for haptic interfaces. Microsyst Nanoeng, 2021, 7, 85, doi:10.1038/s41378-021-00301-x.

Moody, G. B. & Mark, R. G. The impact of the MIT-BIH arrhythmia database. IEEE Eng Med Biol Mag, 2001, 20, 45-50, doi: 10.1109/51.932724.

Jiapu Pan and Willis J. Tompkins, A real-time QRS detection algorithm. 1985, IEEE Transactions On Biomedical Engineering, vol. BME-32, No. 3, M P. 230-236.

Li, T. & Zhou, M. ECG Classification Using Wavelet Packet Entropy and Random Forests. Entropy, 2016, 18, 285, doi:10.3390/e18080285.

A. Bansal and R. Joshi, "Portable out-of-hospital electrocardiograma review of current technologies," (in eng), J Arrhythm, vol. 34, No. 2, pp. 129-138, 2018, doi: 10.1002/joa3.12035.

M. Rimol. "Gartner Forecasts Global Spending on Wearable Devices to Total $81.5 Billion in 2021." https://www.gartner.com/en/newsroom/press-releases/2021-01-11-gartner-forecasts-global-spending-on-wearable-devices-to-total-81-5-billion-in-2021.

Roth, G. A., Mensah, G. A., Johnson, C. O. et al. Global Burden of Cardiovascular Diseases and Risk Factors, 1990-2019: Update From the GBD 2019 Study. J Am Coll Cardiol, 2020, 76, 2982-3021, doi:10.1016/j.jacc.2020.11.010.

Virani, S. S., Alonso, A., Aparicio, H. J. et al. Heart Disease and Stroke Statistics-2021 Update: A Report From the American Heart Association. Circulation, 2021, 143, e254-e743, doi:10.1161/CIR.0000000000000950.

Mensah, G. A., Roth, G. A. & Fuster, V. The Global Burden of Cardiovascular Diseases and Risk Factors: 2020 and Beyond. J Am Coll Cardiol, 2019, 74, 2529-2532, doi:10.1016/j.jacc.2019.10.009.

Grundy, S. M., Balady, G. J., Criqui, M. H. et al. Guide to primary prevention of cardiovascular diseases. A statement for healthcare professionals from the Task Force on Risk Reduction. American Heart Association Science Advisory and Coordinating Committee. Circulation, 1997, 95, 2329-2331, doi: 10.1161/01.cir.95.9.2329.

Karunathilake, S. P. & Ganegoda, G. U. Secondary Prevention of Cardiovascular Diseases and Application of Technology for Early Diagnosis. Biomed Res Int, 2018, 2018, 5767864, doi: 10.1155/2018/5767864.

AlGhatrif, M. & Lindsay, J. A brief review: history to understand fundamentals of electrocardiogrammunity Hosp Intern Med Perspect, 2012, 2, doi:10.3402/jchimp.v2I1.14383.

Bolanos, M., Nazeran, H. & Haltiwanger, E. Comparison of heart rate variability signal features derived from electrocardiogramd photoplethysmography in healthy individuals. Conf Proc IEEE Eng Med Biol Soc, 2006, 2006, 4289-4294, doi:10.1109/IEMBS.2006.260607.

Graatsma, E. M., Jacod, B. C., van Egmond, L. A., Mulder, E. J. & Visser, G. H. Fetal electrocardiogramaasibility of long-term fetal heart rate recordings. BJOG, 2009, 116, 334-337; discussion 337-338, doi: 10.1111/j.1471-0528.2008.01951.x.

Feldman, T., Borow, K. M., Neumann, A., Lang, R. M. & Childers, R. W. Relation of electrocardiogramave R-wave amplitude to changes in left ventricular chamber size and position in normal subjects. The American Journal of Cardiology, 1985, 55, 1168-1174, doi: 10.1016/0002-9149(85)90657-5.

McLenachan, J. M., Henderson, E., Morris, K. I. & Dargie, H. J. Ventricular arrhythmias in patients with hypertensive left ventricular hypertrophy. N Engl J Med, 1987, 317, 787-792, doi: 10.1056/NEJM198709243171302.

Peguero, J. G., Lo Presti, S., Perez, J. et al. Electrocardiogram the Diagnosis of Left Ventricular Hypertrophy. J Am Coll Cardiol, 2017, 69, 1694-1703, doi:10.1016/j.jacc.2017.01.037.

Coisne, A., Ninni, S., Pontana, F. et al. Clinical significance of electrocardiogramarkers of myocardial damage prior to aortic valve replacement. Int J Cardiol, 2020, 307, 130-135, doi: 10.1016/j.ijcard.2020.01.073.

Petrutiu, S., Sahakian, A. V., Ricke, A., Young, B. & Swiryn, S. High Resolution Electrocardiogramised for Recording Pulses from Electronic Pacemakers: Evaluation of a New Pacemaker Sensing System. Comput Cardiol, 2007, 34, 197-+, doi:Doi 10.1109/Cic.2007.4745455.

Das, M. K., Maskoun, W., Shen, C. et al. Fragmented QRS on twelve-lead electrocardiogram predicts arrhythmic events in patients with ischemic and nonischemic cardiomyopathy. Heart Rhythm, 2010, 7, 74-80, doi: 10.1016/j.hrthm.2009.09.065.

(56) References Cited

OTHER PUBLICATIONS

Larsen, R. L., Jakacki, R. I., Vetter, V. L. et al. Electrocardiogramanges and arrhythmias after cancer therapy in children and young adults. The American Journal of Cardiology, 1992, 70, 73-77, doi:10.1016/0002-9149(92)91393-i.

Charya, U. R., Fujita, H., Lih, O. S. et al. Automated detection of arrhythmias using different intervals of tachycardia ECG segments with convolutional neural network. Information Sciences, 2017, 405, 81-90, doi:10.1016/j.ins.2017.04.012.

Spann, J. F., Jr., Moellering, R. C., Jr., Haber, E. & Wheeler, E. O. Arrhythmias in Acute Myocardial Infarction; a Study Utilizing an Electrocardiogramonitor for Automatic Detection and Recording of Arrhythmias. N Engl J Med, 1964, 271, 427-431, doi: 10.1056/NEJM196408272710901.

Steinberg, J. S., Zelenkofske, S., Wong, S. C. et al. Value of the P-wave signal-averaged ECG for predicting atrial fibrillation after cardiac surgery. Circulation, 1993, 88, 2618-2622, doi: 10.1161/01.cir.88.6.2618.

Fukunami, M., Yamada, T., Ohmori, M. et al. Detection of patients at risk for paroxysmal atrial fibrillation during sinus rhythm by P wave-triggered signal-averaged electrocardiogram. Circulation, 1991, 83, 162-169, doi: 10.1161/01.cir.83.1.162.

Mittal, S., Movsowitz, C. & Steinberg, J. S. Ambulatory external electrocardiogrammonitoring: focus on atrial fibrillation. J Am Coll Cardiol, 2011, 58, 1741-1749, doi:10.1016/j.jacc.2011.07.02.

Peeters, H. A., Sippensgroenewegen, A., Wever, E. F. et al. Electrocardiogramtification of abnormal ventricular depolarization and repolarization in patients with idiopathic ventricular fibrillation. J Am Coll Cardiol, 1998, 31, 1406-1413, doi:10.1016/s0735-1097(98)00120-x.

Amit, G., Granot, Y. & Abboud, S. Quantifying QRS changes during myocardial ischemia: Insights from high frequency electrocardiography. J. Electrocardial, 2014, 47, 505-511, doi: 10.1016/j.jelectrocard.2014.03.006.

Fleg, J. L., Gerstenblith, G., Zonderman, A. B. et al. Prevalence and prognostic significance of exercise-induced silent myocardial ischemia detected by thallium scintigraphy and electrocardiogram asymptomatic volunteers. Circulation, 1990, 81, 428-436, doi:10.1161/01.cir.81.2.428.

Zimetbaum, P. J. & Josephson, M. E. Use of the electrocardiogram in acute myocardial infarction. N Engl J Med, 2003, 348, 933-940, doi: 10.1056/NEJMra022700.

Sgarbossa, E. B., Pinski, S. L., Barbagelata, A. et al. Electrocardiogramagnosis of evolving acute myocardial infarction in the presence of left bundle-branch block. GUSTO-1 (Global Utilization of Streptokinase and Tissue Plasminogen Activator for Occluded Coronary Arteries) Investigators. N Engl J Med, 1996, 334, 481-487, doi: 10.1056/NEJM199602223340801.

Michaelides, A. P., Psomadaki, Z. D., Dilaveris, P. E. et al. Improved detection of coronary artery disease by exercise electrocardiograma use of right precordial leads. N Engl J Med, 1999, 340, 340-345, doi: 10.1056/NEJM199902043400502.

Brugada, J., Brugada, R. & Brugada, P. Determinants of sudden cardiac death in individuals with the electrocardiogram of Brugada syndrome and No. previous cardiac arrest. Circulation, 2003, 108, 3092-3096, doi:10.1161/01.CIR.0000104568.13957.4F.

Gussak, I., Antzelevitch, C., Bjerregaard, P., Towbin, J. A. & Chaitman, B. R. The Brugada syndrome: clinical, electrophysiologic and genetic aspects. J Am Coll Cardiol, 1999, 33, 5-15, doi:10.1016/s0735-1097(98)00528-2.

Brugada, J., Campuzano, O., Arbelo, E., Sarquella-Brugada, G. & Brugada, R. Present Status of Brugada Syndrome: JACC State-of-the-Art Review. J Am Coll Cardiol, 2018, 72, 1046-1059, doi: 10.1016/j.jacc.2018.06.037.

Li, R. A., Leppo, M., Miki, T., Seino, S. & Marban, E. Molecular basis of electrocardiogramaegment elevation. Circ Res, 2000, 87, 837-839, doi:10.1161/01.res.87.10.837.

Oresko, J. J., Zhanpeng, J., Jun, C. et al. A Wearable Smartphone-Based Platform for Real-Time Cardiovascular Disease Detection Via Electrocardiogram Processing. IEEE Transactions on Information Technology in Biomedicine, 2010, 14, 734-740, doi:10.1109/titb.2010.2047865.

Harrison, D. C., Fitzgerald, J. W. & Winkle, R. A. Ambulatory electrocardiogramar diagnosis and treatment of cardiac arrhythmias. N Engl J Med, 1976, 294, 373-380, doi:10.1056/NEJM197602122940706.

Andesberg, G. Monitoring for myocardial ischemia. Best Practice & Research Clinical Anaesthesiology, 2005, 19, 77-95, doi: 10.1016/j.bpa.2004.07.006.

Lou, C., Li, R., Li, Z. et al. Flexible graphene electrodes for prolonged dynamic ECG monitoring. Sensors, 2016, 16, 1833.

Zahed, M. A., Das, P. S., Maharjan, P. et al. Flexible and robust dry electrodes based on electroconductive polymer spray-coated 3D porous graphene for long-term electrocardiogram signal monitoring system. Carbon, 2020, 165, 26-36.

Bonek, L., Fenech, S., Sapoznik, N. et al. "Development of a Flexible and Wireless ECG Monitoring Devicen" in 2020 IEEE Sensors. 1-4 (IEEE).

Yamamoto, Y., Yamamoto, D., Takada, M. et al. Efficient skin temperature sensor and stable gel-less sticky ECG sensor for a wearable flexible healthcare patch. Advanced healthcare materials, 2017, 6, 1700495.

Lee, S. M., Byeon, H. J., Lee, J. H. et al. Self-adhesive epidermal carbon nanotube electronics for tether-free long-term continuous recording of biosignals. Scientific reports, 2014, 4, 1-9.

Stauffer, F., Thielen, M., Sauter, C. et al. Skin conformal polymer electrodes for clinical ECG and EEG recordings. Advanced healthcare materials, 2018, 7, 1700994.

Ji, S., Wan, C., Wang, T. et al. Water-resistant conformal hybrid electrodes for aquatic endurable electrocardiographic monitoring. Advanced Materials, 2020, 32, 2001496.

Salvo, P., Raedt, R., Carrette, E. et al. A 3D printed dry electrode for ECG/EEG recording. Sensors and Actuators A: Physical, 2012, 174, 96-102, doi:10.1016/j.sna.2011.12.017.

Bumgarner, J. M., Lambert, C. T., Hussein, A. A. et al. Smartwatch Algorithm for Automated Detection of Atrial Fibrillation. J Am Coll Cardiol, 2018, 71, 2381-2388, doi:10.1016/j.jacc.2018.03.003.

Mehta, D. D., Nazir, N. T., Trohman, R. G. & Volgman, A. S. Single-lead portable ECG devices: Perceptions and clinical accuracy compared to conventional cardiac monitoring. J Electrocardiol, 2015, 48, 710-716, doi: 10.1016/j.jelectrocard.2015.04.017.

Jabaudon, D., Sztajzel, J., Sievert, K., Landis, T. & Sztajzel, R. Usefulness of ambulatory 7-day ECG monitoring for the detection of atrial fibrillation and flutter after acute stroke and transient ischemic attack. Stroke, 2004, 35, 1647-1651, doi:10.1161/01.STR.0000131269.69502.d9.

Crawford, M. H., Bernstein, S. J., Deedwania, P. C. et al. ACC/AHA guidelines for ambulatory electrocardiography: executive summary and recommendations. A report of the American College of Cardiology/American Heart Association task force on practice guidelines (committee to revise the guidelines for ambulatory electrocardiography). Circulation, 1999, 100, 886-893, doi:10.1161/01.cir. 100.8.886.

Larsen, M. P., Eisenberg, M. S., Cummins, R. O. & Hallstrom, A. P. Predicting survival from out-of-hospital cardiac arrest: A graphic model. Annals of Emergency Medicine, 1993, 22, 1652-1658, doi: 10.1016/s0196-0644(05)81302-2.

Chan, P. S., Krumholz, H. M., Nichol, G., Nallamothu, B. K. & American Heart Association National Registry of Cardiopulmonary Resuscitation, I. Delayed time to defibrillation after in-hospital cardiac arrest. N Engl J Med, 2008, 358, 9-17, doi: 10.1056/NEJMoa0706467.

Anuradha, B., Reddy, V. V. J. A. J. o. E. & Sciences, A. ANN for classification of cardiac arrhythmias. 2008, 3, 1-6.

* cited by examiner

Two-layer Electrode

STRETCHABLE AND WEARABLE WIRELESS 3-LEADS ECG MONITORING APPARATUS

CROSS-REFERENCE WITH RELATED APPLICATIONS

This application claims priority to the U.S. Provisional Patent Application No. 63/214,308 filed Jun. 24, 2021; the disclosure of which is incorporated herein by reference in its entirety.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to wireless monitors in general and, more particularly, to flexible and wearable wireless monitors capable of monitoring electrocardiogram (ECG) signals.

BACKGROUND

Cardiovascular diseases (CVDs) led to approximately 20 million deaths globally each year. Behavioral risk factors addressing and early diagnosis, including the application of specific medical instruments, are vital for CVDs prevention. Precisely focusing on this issue, electrocardiography (ECG) shows its irreplaceable value in demonstrating physiological information related to CVDs, including (1) structure of the heart and function of its electrical conduction system; (2) rate and rhythm of heartbeats; (3) size and position of the heart chambers; (4) presence of a damaged area of cardiomyocyte; and (5) medical influence towards the heart function and operational condition of implanted pacemakers.

Credit to the advancement of recent technologies, a wide variety of CVDs could be accurately diagnosed by analyzing ECG signals, including but not limited to cardiac arrhythmias, atrial fibrillation, ventricular fibrillation, myocardial ischemia, myocardial infarction, coronary artery disease, and Brugada syndrome. Take myocardial ischemia as an example, by recognizing the ST-segment elevations and depressions in ECG signals, CVDs could be detected and prevented in the early stages. It is proven that continuous ECG signals monitoring plays an essential role among patients who suffer from CVDs or have high cardiovascular risk.

Up to now, there are two types of ECG monitoring devices based on the number of leads being used: single-lead ECG and multi-leads ECG (ranging from 2 to 12 leads). Commercialized wearable single-lead ECG devices, which could provide accurate heart rate (HR) measurement, are a mature technology in the market, such as fitness trackers and smartwatches. However, these devices could not provide sufficient medical information and professional disease diagnosis apart from the HR monitoring. It has been reported that over 40% of the wearable ECG rhythms measured by single-lead ECG devices are uninterpretable signals while only 50% of the signals match with those from obtained from a hospital cardiac monitor. Compared with portable single-lead ECG devices, multi-leads ECG devices show advantages of higher diagnostics capability and therefore are widely used in clinical applications. However, almost all multi-leads ECG devices are based on rigid platforms and require stable performing conditions. Thus, using multi-leads ECG devices in ambulatory and other continuous, long-term ECG monitoring conditions is a rather un-user-friendly approach.

Therefore, there is a need in the art for a ECG device that is easy to use, can be worn over a longer period by a subject user, yet reliable and accurate enough for disease diagnosis.

CVD warning system can bring substantial improvements in CVD motility reduction by delivering feedback to the subject user when a fatal cardiac arrest that needs immediate medical treatment is predicted. While the intensity of the warning system's feedback as an indication of the CVD severity may assist the subject users and medical service providers to choose the suitable treatments, the state-of-the-art wearable single-lead and multi-leads ECG devices have no integrated CVD warning system. The rapid development of computing technologies also facilitates data analysis and intelligent diagnosis of heart diseases. Machine learning is a popular technique used for computer-aided diagnosis. Researchers have explored numerous machine learning-based approaches for CVD diagnosis. Although traditional classifiers, such as those based on artificial neural networks (ANNs), support vector machines (SVM), random forest, and other simple algorithms have low computing cost, deep learning techniques have higher diagnostic accuracy and does not require the time-consuming feature engineering associated with traditional classifiers. Therefore, the integration of deep learning models for arrhythmia classification may further increase the diagnostic accuracy of a ECG-based CVD monitoring system.

SUMMARY OF THE INVENTION

It is an objective of the present invention to provide a 3-leads ECG system that is easy to use for long-period monitoring and disease diagnosis. It is a further objective of the present invention in that the 3-leads ECG system addresses the aforementioned shortcomings of the prior arts by providing that: (1) the wearable portion of the 3-leads ECG system being built with flexible substrates integrating flexible electronics capable of stretching, bending, and twisting repeatedly under extreme external loads induced by its wearer's motions; (2) the 3-leads ECG system being able to capture clear multi-leads ECG signals of a subject user in a continuous and stable manner; (3) the 3-leads ECG system incorporating a vibration feedback mechanism for cardiac abnormalities warning and CVD severeness indication; and (4) the 3-leads ECG system integrating with deep learning models for CVD classification for high-accuracy prediction of CVD.

In accordance to one embodiment of the present invention, the 3-leads ECG system comprises: a stretchable and flexible main patch containing a primary circuitry; four leads; and an electronic user interface (UI).

The main patch contains the primary circuitry and is fabricated on a soft substrate. The four leads are connected to the primary circuitry. The wires of the four leads are encapsulated by thin polydimethylsiloxane (PDMS) layers, which provide both electrical insulation, noise reduction, and flexibility.

In one embodiment, four commercially available disposable ECG electrode patches are used and each is connected to the end of each of the four leads. Each of the ECG electrode patches is placed on one of the human torsos, including the right arm (RA), left arm (LA), left leg (LL), and right leg (RL), of the subject user. The RL lead is a neutral lead for actively cancelling the interference noise and plays no role in the ECG signal measurement itself. As a result, the measurement is actually based on three leads. In other embodiments, the three different measurement leads are not only limited to limb leads. The measurement leads can be adjusted in other positions according to the application and medical specialist's recommendation.

The primary circuitry comprises two layers of soft printed circuit stacked on each other, forming a two-layer soft printed circuit. The top layer includes electronic components and conductive (i.e., copper) traces, and the bottom layer has additional conductive traces, completing the connections among the components on the top layer. Traces on the two layers are connected using conductive metal (i.e., silver) paste. As a result, the primary circuitry, contained within the main patch, is an entirely flexible and stretchable ECG front-end circuit attached to the subject user's body when used.

In one embodiment, the 3-leads ECG system further comprises a soft vibration actuator embedded in the main patch for delivering a tactile alarm to the subject user. The primary circuitry is further configured to drive the actuator by transmitting to it pulse-width modulation signals for detections of abnormality in the measured ECG signals as analyzed by the primary circuitry or the electronic UI. By the vibration of the actuator, the subject user is notified of the abnormal ECG so to seek timely medical attention, achieving the monitoring function of the 3-leads ECG system.

Lastly; the measured ECG signal data is transmitted by the primary circuitry via wire or wirelessly to the electronic UI, which may be implemented by; without limitation, a personal computer, a mobile computer, tablet computer, a mobile phone, kiosk, or any other computing device capable of conducting data communication with the device, processing and displaying the received measured ECG signal data on an electronic display in real-time.

BRIEF DESCRIPTION OF THE DRAWINGS

Embodiments of the invention are described in more details hereinafter with reference to the drawings, in which.

DETAILED DESCRIPTION

Figure 1A:
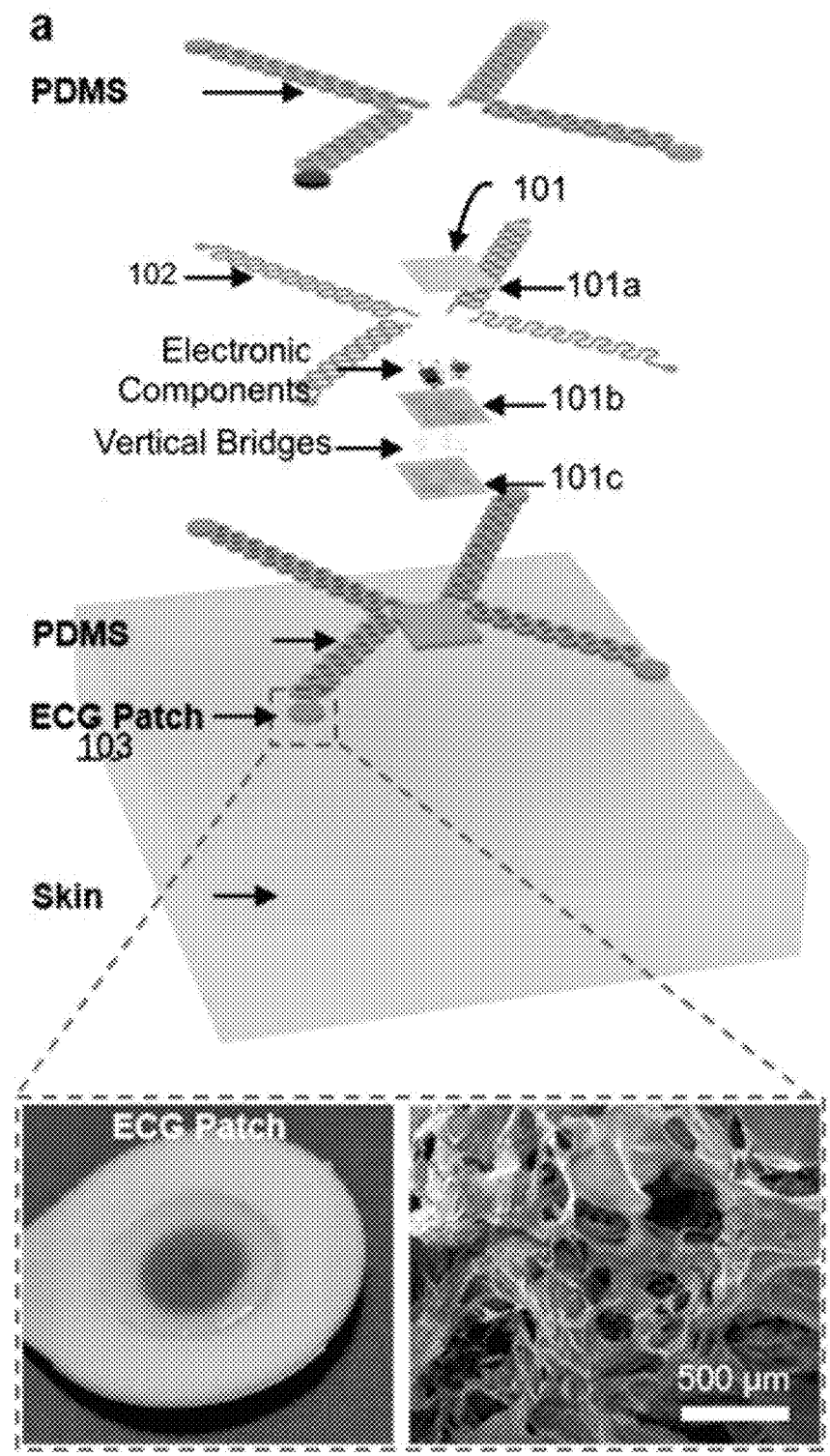
FIG. 1a depicts a schematic diagram illustrating a 3-leads ECG system in accordance with one embodiment of the present invention.

In the following description, methods, electronic devices, and systems for long period ECG monitoring and disease diagnosis and the likes are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

In accordance to one aspect of the present invention, provided is a 3-leads ECG system capable of receiving and monitoring a 3-leads ECG signal and easy to use for long period monitoring purposes and is sufficiently reliable for disease diagnosis.

Referring to FIGS. 1a, 1b, 1c, and 1d for the following description. In accordance to one embodiment of the present invention, the 3-leads ECG system comprises a stretchable and flexible main patch 101 containing a primary circuitry; four leads 102 connected to the primary circuitry of the main patch 101; and an electronic user interface (UI).

In one embodiment, each of the four leads 102 comprises a conductive (i.e., copper) wire. The four leads 102 may have different lengths. In an exemplary embodiment, the length for the LA and RA connecting leads is 14 cm, and the length for the LL and RL connecting leads is 10 cm. Each wire is encapsulated by a thin layer of PDMS, which is a flexible and stretchable polymer. The encapsulation layer provides the needed flexibility for the four leads 102 while offering electrical isolation and in turn noise reduction.

The 3-leads ECG system further comprises four ECG electrode patches 103. In one embodiment, commercially available disposable ECG electrode patches (i.e., Tianrun Sunshine™ disposable electrode button ECG electrode patch, YH-1, Ag/AgCl) are used. Each ECG electrode patch 103 is connected to the end of each of the four leads 102 and attached to one of the human torsos (i.e., RA, LA, LL, and RL) of the subject user. Under one configuration, the RL lead is a neutral lead for actively cancelling the interference noise and plays no role in the ECG signal measurement itself. As a result, the measurement is actually based on three leads. In other embodiments, the three different measurement leads are not only limited to limb leads. The measurement leads can be adjusted in other positions according to the application and medical specialist's recommendation.

In another embodiment; the ECG electrode patches are organohydrogel ECG electrode patches. The organohydrogel material is fabricated by a photo-triggered gelation procedure in a binary solvent of glycerol-water. In more details, the photo-triggered gelation procedure comprises adding 1 g gelatin into 9 ml deionized water; stirring the mixture at 60° C. for 2 hour to produce 3 ml gelatin (10 wt %) solution; then, adding 2.1 g SRMA, 0.9 g AAc, 5 mg MBAA, 50 mg 2959, 0.33 g CaCl2, and 3 ml glycerol into the 3 ml gelatin (10 wt %) solution to produce a mixed solution; then degassing the mixed solution for 30 min, followed by placing it at illumination of IN light for 30 minutes to produce the organohydrogel the ionic polymer skeleton of the ECG electrode patches. The organohydrogel ECG electrode patches have significantly higher sustained conductivity than most commercially available ECG electrode patches. The organohydrogel ECG electrode patches also deliver much more robust adhesion strength than commercially available ECG electrode patches do. As can be seen in the exploded view and scanning electron microscope (SEM) image of an ECG electrode patch 103 in FIG. 1a, the organohydrogel ECG electrode patch has a rough surface indicating high viscosity, allowing it being attached on human skin surface tightly.

Figure 1B:
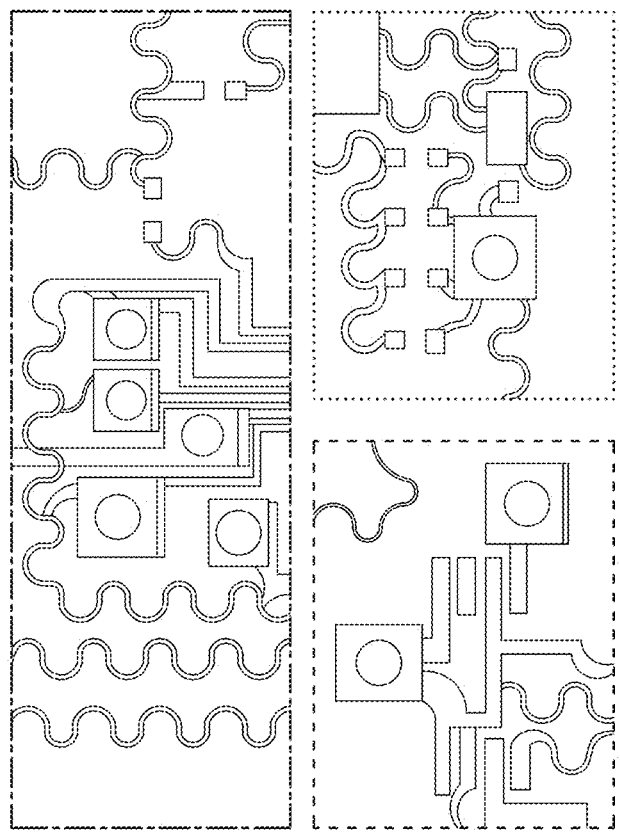
FIGS. 1b and 1c depict the exploded views of a primary circuitry of the 3-leads ECG system.
Figure 1B:
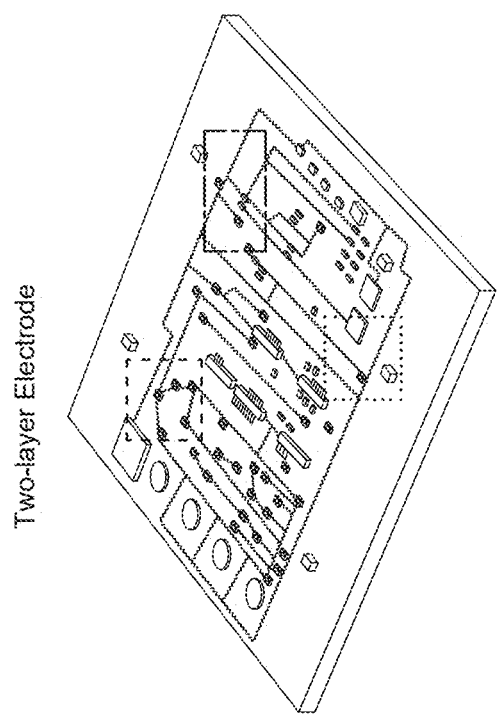
Figure 1C:
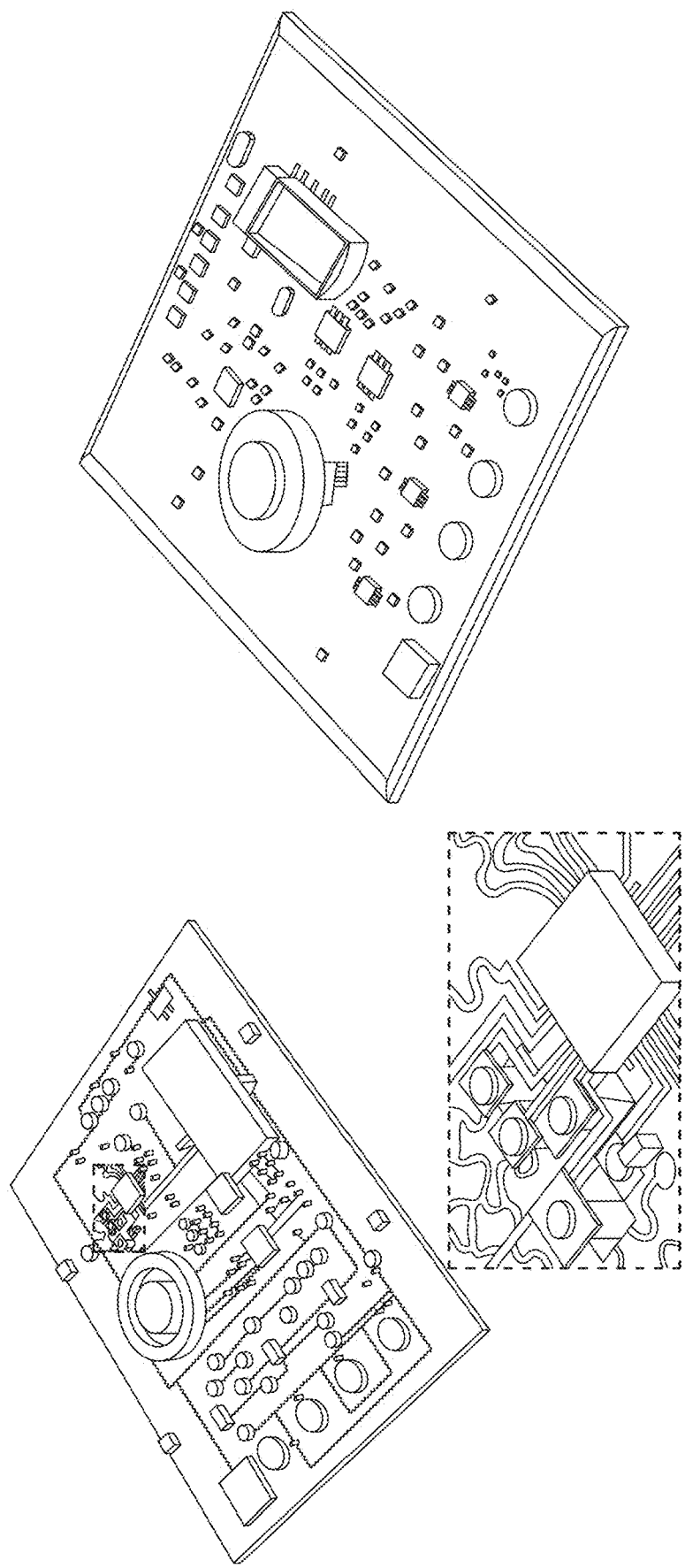
Figure 1D:
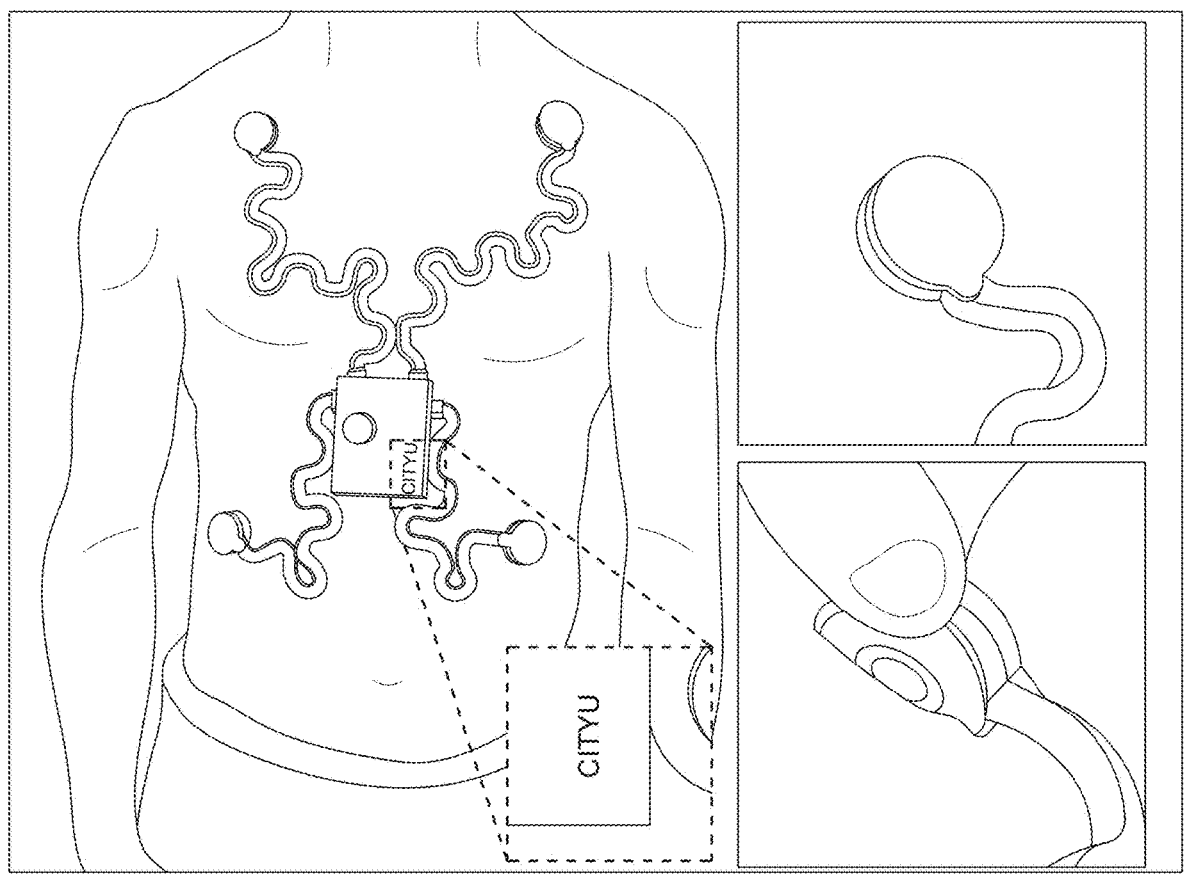
FIG. 1d depicts the 3-leads ECG system being worn on the body of a subject user.

In one embodiment, the main patch contains the primary circuitry and is fabricated on a stretchable and flexible substrate. Thus, the main patch comprises three layers of PDMS, one layer being the stretchable and flexible substrate 101a, and the other two serving as the top and bottom electrode layers 101b and 101c for the printed circuit board implementations of the primary circuitry. An exploded view of the primary circuitry is shown in FIGS. 1b and 1c. The top and bottom electrode layers 101b and 101c of the primary circuit are stacked on each other, forming a two-layer soft printed circuit. Thus, the primary circuitry comprises the top electrode layer 101b, which further contains electronic components and conductive (i.e., copper) traces; and the bottom electrode layer 101c containing additional conductive traces for completing the connections among the elements on the top electrode layer 101b. The conductive traces on the two layers are connected using conductive (i.e., silver) paste. As can be seen in FIGS. 1b and 1c, the layouts of the conductive traces are in interconnecting serpentine shape. This is so to allow them to be stretchable, bendable, and twistable.

Figure 2A:
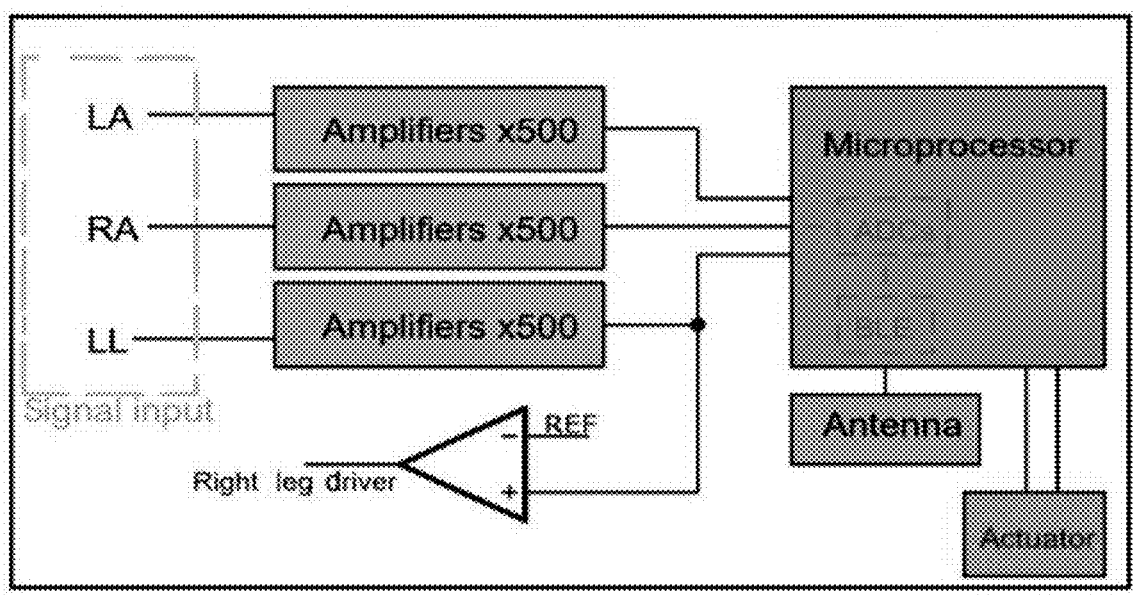
FIG. 2a depicts a schematic diagram illustrating the electronic components and their interconnections in the primary circuitry in accordance with one embodiment of the present invention.

The electronic components may include, but not limited to, an user control panel having electro-mechanical buttons and/or switches for controlling the various functions of the ECG system, such as power on/off, activate/deactivate alarm, enable/disable wireless communication, and pairing/unpairing with external Bluetooth devices; a microcontroller configured to process the measured ECG signal received from the measurement leads, process control signals received from the user control panel and/or the electronic UI, facilitate data communication with the electronic and communication under the Bluetooth protocol with external devices, and drive a vibration actuator, wherein the microcontroller includes an integrated analog-to-digital converter (ADC) (i.e., 12-bit ADC) for converting the analog measured ECG signal received from the measurement leads to digital values for processing, and an integrated data communication module (i.e., Bluetooth low energy (BLE) module); a wireless communication antenna connected to the microcontroller; a voltage regulator; one or more instrumentation amplifiers; one or more operational amplifiers; one or more capacitors; one or more resistors; one or more inductance; a vibration actuator for tactile alarm; and a battery, which can be a rechargeable Lipo battery, for powering the primary circuitry. FIG. 2a illustrates the interconnections of some of the aforementioned electronic components.

Figure 2B:
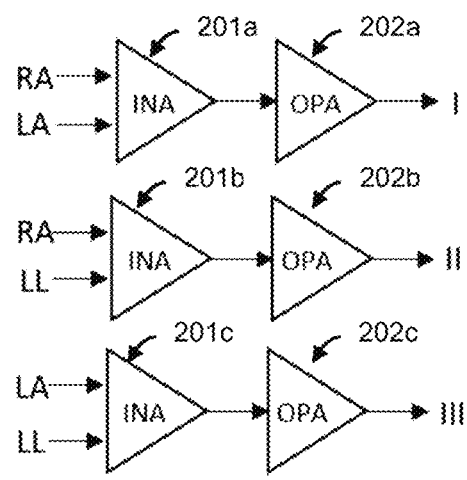
FIG. 2b depicts a schematic diagram illustrating the amplifiers in the primary circuitry for amplifying measured ECG signals received from measurement leads in accordance with one embodiment of the present invention.
Figure 3A:
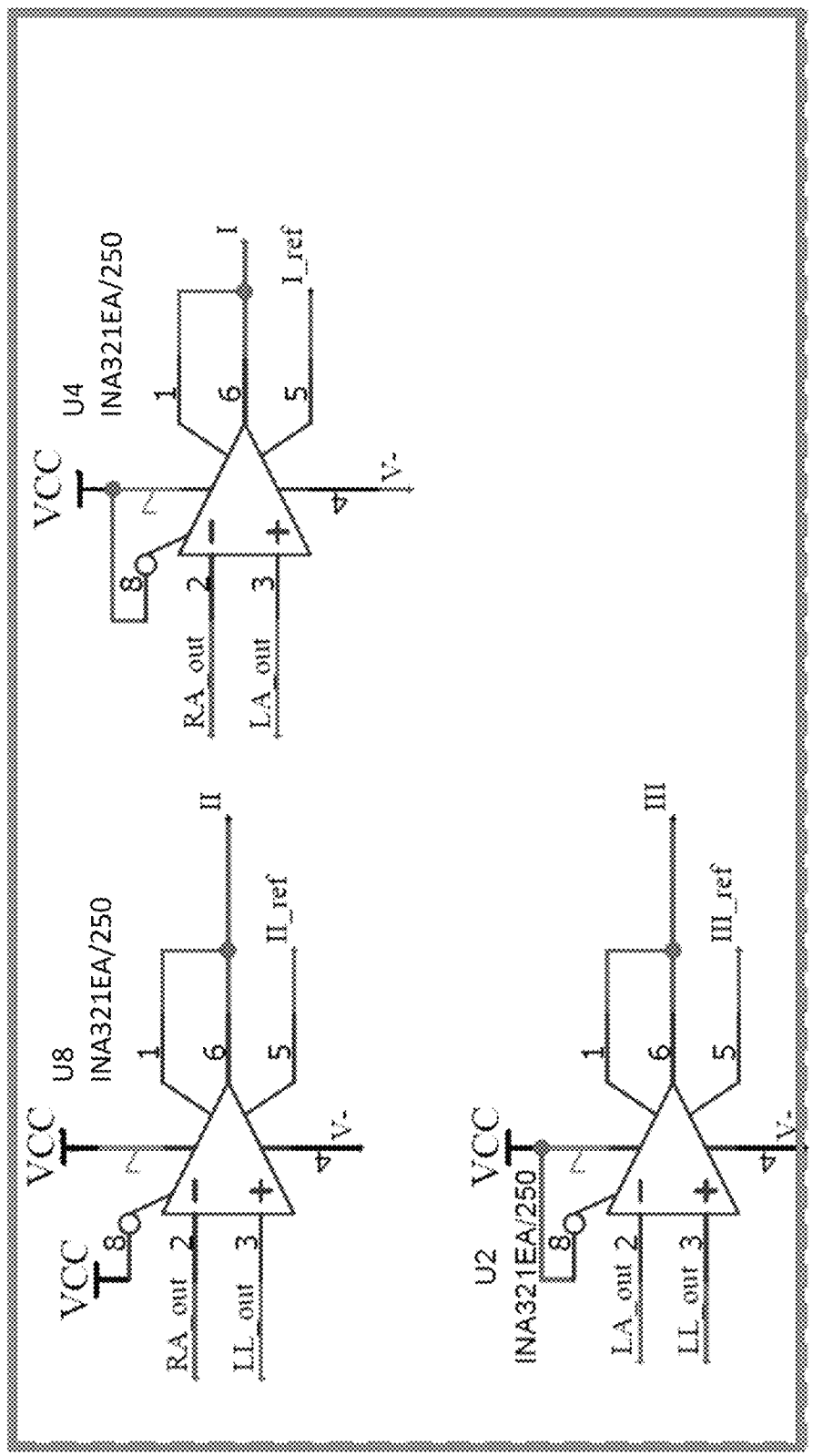
FIGS. 3a-3d depict the circuit diagrams of an exemplary implementation of the primary circuitry.
Figure 3B:
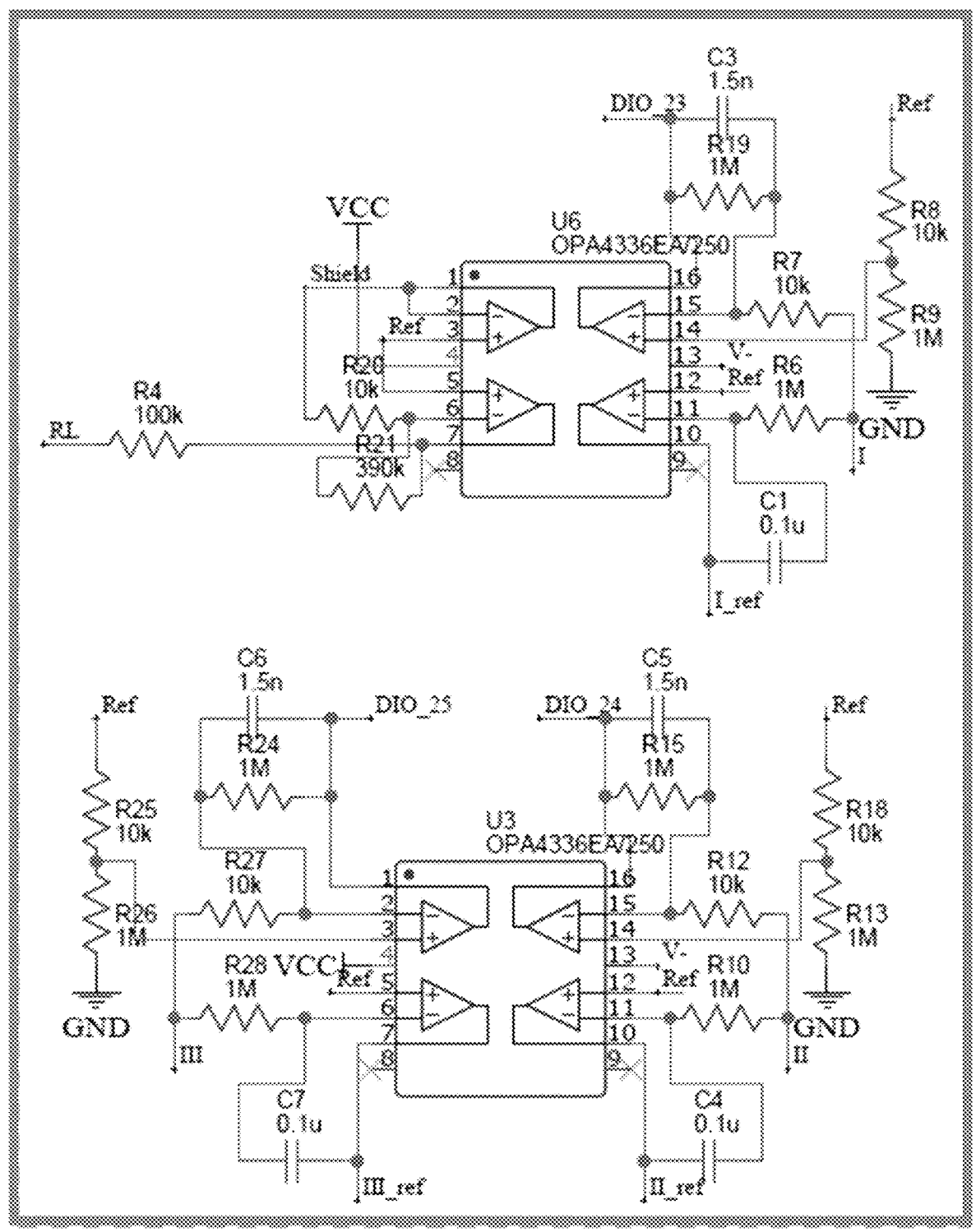
Figure 3C:
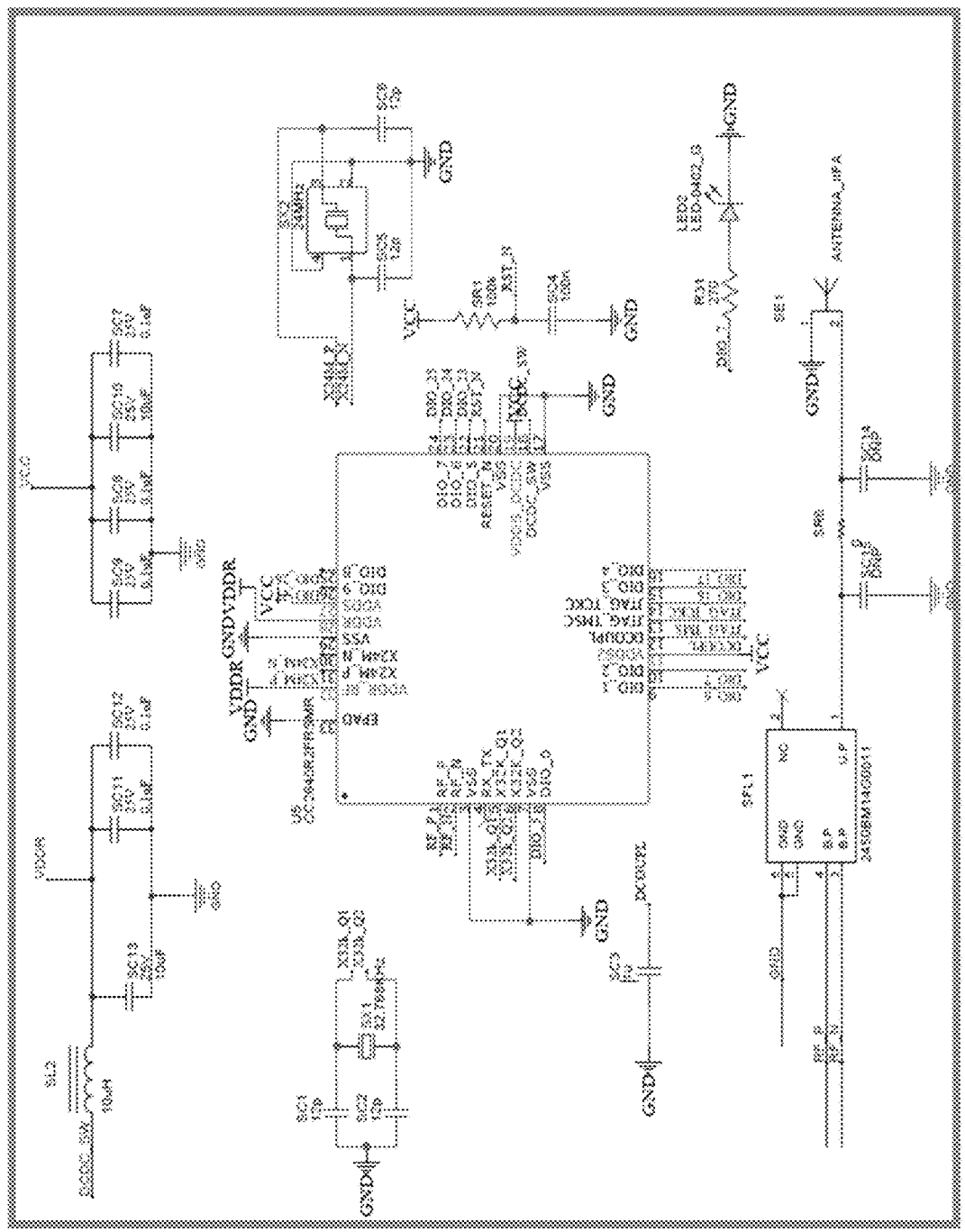
Figure 3D:
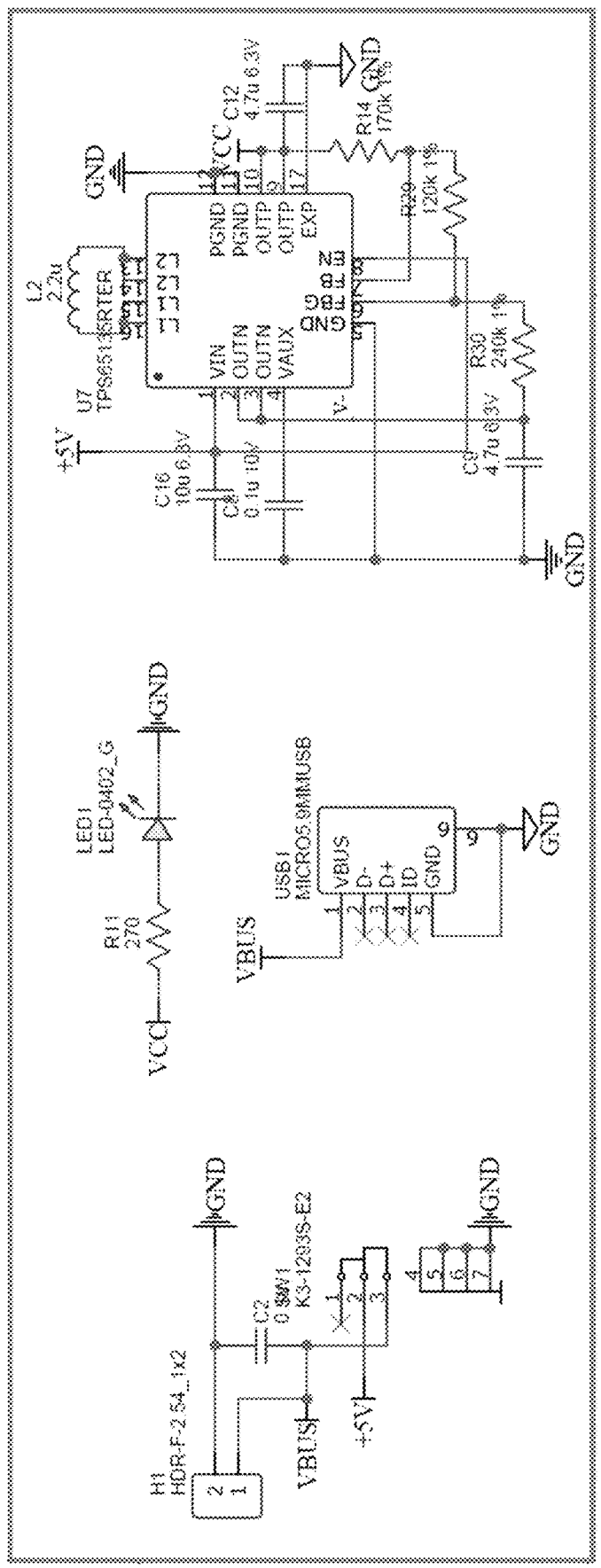

Referring to FIG. 2b for the following description. In one embodiment, the primary circuitry further comprises three instrumentation amplifiers (INAS) 201a, 201b, and 201c for simultaneously amplifying the measured ECG signals received from the three measurement leads. The INAs offer very high input impedance and a high common-mode rejection ratio, making them suitable for bio-signal measurements. The first INA 201a takes as input the measured ECG signals received from the RA measurement lead and the LA measurement lead; the second INA 201b takes as input the measured ECG signals received from the RA measurement lead and the LL measurement lead; and third INA 201c takes as input the measured ECG signals received from the LA measurement lead and the LL measurement lead. The primary circuitry further comprises three operational amplifiers (OPAs) 202a, 202b, and 202c. The inputs of the OPAs 202a, 202b, and 202c are connected to the outputs of the INAs 201a, 201b, and 201c respectively, and are configured to amplify the outputs of the INAs. Each of the OPAs further includes a compensation capacitor for phase shift compensation. Additionally, due to the gain bandwidth (GBW) of the OPAs and the sampling frequency, a low pass filter with a cut-off frequency at 500 Hz is formed. As a result, the measured ECG signal received from each of the ECG measurement leads is amplified by a gain of 500 through the INAs and the OPAs.

In biopotential measurements, rejecting common-mode voltage always is a challenge. One solution is to apply a dynamic feedback signal to the body of the subject user to reduce the common-mode interference, maintaining the common-mode voltage stability of the subject user's body. This dynamic feedback signal is achieved through a resister-inductor-diode (RLD) circuit by obtaining an average of the three measured ECG signal voltage readings from the ECG measurement leads and a reference voltage. The dynamic feedback signal is then the difference between the average of the three measured ECG signal voltage readings and the reference voltage for applying to one of the subject user's torsos via the neutral lead. The RLD circuit uses an operational amplifier as the buffer and another one in order to amplify the difference before applying it to the body.

In one embodiment, the 3-leads ECG system further comprises a soft vibration actuator embedded in the main patch for delivering a tactile alarm to the subject user. The primary circuitry is further configured to drive the actuator by transmitting to it pulse-width modulation driving signals for detections of abnormality in the measured ECG signals as analyzed by the primary circuitry, the electronic UI, or another external computing device. The vibration actuator has a multilayer structure including a copper coil, a polyethylene terephthalate film, a magnet sheet, and a three-dimensional (3D)-printed ring.

In one embodiment, the main patch 101 with its primary circuitry are fabricated by the process described below.

Taking the bottom electrode layer 101c of the primary circuitry first. First, a piece of quartz glass (i.e., 75×75 mm), cleaned with acetone, alcohol, and deionized water (DI water), is applied as a supporting layer. A little sodium stearate aqueous solution was spin-coated on the quartz glass then dried under 100° C. for 5 minutes, forming as a thin sacrificial layer for later flaking the above materials. Then, a PDMS film (i.e., ~0.17 mm) is spin-coated on the quartz glass trip at 600 r/min for 30 second, then baked at 110° C. for 5 minutes. The PDMS film acts as the stretchable and flexible substrate for the main patch. Next, a copper circuit layer is to be attached to the PDMS film. To ensure tight adhesion strength between the copper circuit layer and the PDMS film, another ultrathin PDMS film is spread over the PDMS film before attaching a polyimide PI-supported copper sheet to it. After attaching the PI (i.e., 12 μm thick)—supported copper (i.e., 6 μm thick) sheet to the PDMS film, baking the sample at 110° C. for 5 minutes to dry the middle-layered ultrathin PDMS film. Spin-coating the PDMS film separately controls the entire thickness of the combined layers and the tight adhesion between the PI-supported copper sheet and the underneath PDMS film. Then, a printed circuit on the PI-supported copper sheet is ready to be patterned by photolithography and etching, yielding metal trace in the designed pattern. A positive photoresist (PR) (i.e., AZ 4620, AZ Electronic Materials) is spin-coated on to the PI-supported copper sheet at 3000 r/min for 30 seconds, baked on a hot plate at 110° C. for 5 min, then exposed to ultraviolet (UV) light for 45 seconds, with a mask of the pattern. After being exposed to the UV light, the printed circuit is developed for 1 minute in a solution (i.e., AZ 400 K) to remove the undesired PR and developed in a Fe2O3 solution for etching the unwanted copper. After development, the was removed by acetone and rinsed with DI water to clean the entire combined layers, completing the fabrication of the bottom electrode layer 101c.

After fabrication of the bottom electrode layer 101c, another one thin layer of PDMS (i.e., 50 μm) was spin-coated (i.e., 1,000 r/min for 60 second) onto the patterned copper traces. Another PI-supported copper sheet is attached on top of it with markers of the circuit of the top electrode layer 101c exposing for the second alignment. The fabrication process of the top electrode layer 101b is substantially the same as that of the bottom electrode layer 101c with top electrode layer 101b stacking on top of the bottom electrode layer 101c.

After the fabrication of both the top electrode layer 101b and bottom electrode layer 101c, the thin layers of PDMS on top of the patterned copper traces are carefully torn off at the vertical bridge between the top electrode layer and bottom electrode layer copper traces through a high-precision tweezer. Silver paste is filled in for realizing the vertical bridge. Low-temperature solder joints are applied for bonding and electrically connecting other electronic components. The electronic components may include a Bluetooth-enabled low-energy, microcontroller (i.e., CC2640R2FRSMR, Texas Instruments™, Inc.), a wireless communication antenna. (i.e., 2450AT18A100E), a voltage regulator (i.e., TPS76933DBVR), one or more instrumentation amplifiers (i.e., INA321EA/250, Texas Instruments Inc.), one or more operational amplifiers (i.e., OPA4336EA/250, Texas Instruments™, Inc.), capacitors (i.e., 0402), resistors (i.e., 0402), inductance (i.e., 0402), and a rechargeable lithium-ion polymer battery (i.e., 3.7V 80 mAh 401020 Li-Po Ion Rechargeable Battery, Liter Energy Battery), The four wires of the four leads are also soldered on to contact pads of the PI-supported copper sheets. Finally, the entire stack of top electrode layer 101b and bottom electrode layer 101c is fixed into a fabricated 3D printing mold, colored PDMS (i.e., 145 kPa, 0.17 mm thick) is poured onto the electronics, followed by curing at 21° C. for 24 hour for solidification. The result is a main patch of the ECG system that measures i.e., 7 cm×6 cm with a thickness of 1 mm, biocompatible, and can be worn on the body of the subject user for extended period of time.

In one embodiment, after the measured ECG signals are received and processed, including a conversion from analog to digital data, by the primary circuitry, the measured ECG signal data are transmitted via wire or wirelessly to the electronic UI for further processing, recording, and displaying. In one embodiment, the further processing comprises applying additional filters to the measured ECG signal data. These filters include an FIR low-pass filter and an FIR notch filter. A simple operation of five points averaging forms a low-pass filter with a cut-off frequency of 100 Hz, thus eliminating high-frequency noise while preserving all valuable information in the measured ECG signal data's specified bandwidth. The FIR notch filter is applied to the measured ECG signal data in order to reduce the power line interference component of 50 Hz.

Figure 4A:
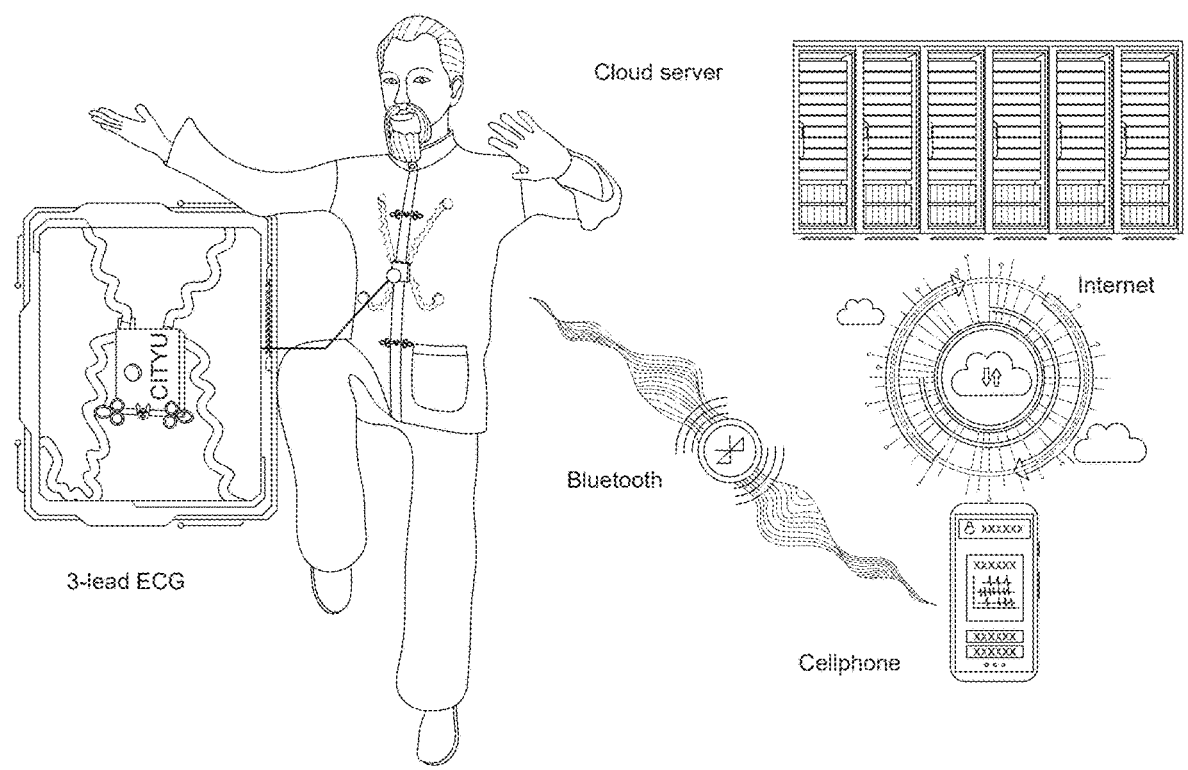
FIG. 4a depicts an illustration of a use scenario of the 3-leads ECG system.
Figure 4B:
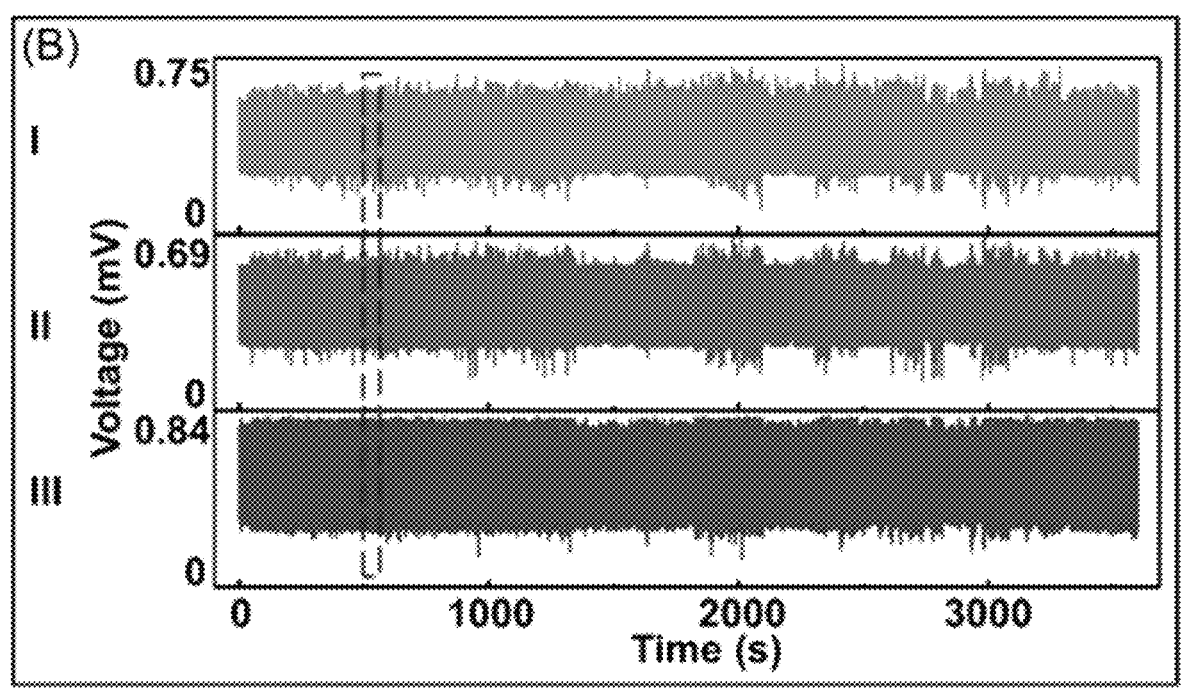
FIGS. 4b and 4c depict two exemplary information displays by an electronic user interface (UI) of the 3-leads ECG system.
Figure 4C:
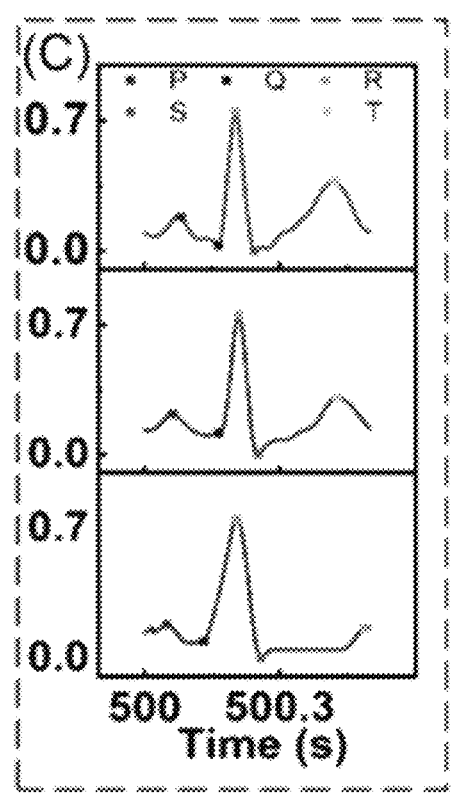

The electronic VI may be implemented the electronic UI, which may be implemented by, without limitation, a personal computer, a mobile computer, tablet computer, a mobile phone, kiosk, or any other computing device capable of conducting data communication with the primary circuitry, processing and displaying the received measured ECG signal data on an electronic display in real-time. FIGS. 4b and 4c depict two exemplary information display (one-hour continuous measured ECG signal data with enlarged detail showing P, Q, R, S, and T complexes) by the electronic UI after processing.

In accordance with another aspect of the present invention, analysis of the measured ECG signal data received from the primary circuitry of the 3-leads ECG system is performed by the electronic UI for detections of abnormality in the measured ECG signals. If an abnormality is detected, the electronic UI sends the primary circuitry a control signal for it to activate and drive the vibration actuator to alert the subject user.

Figure 5:
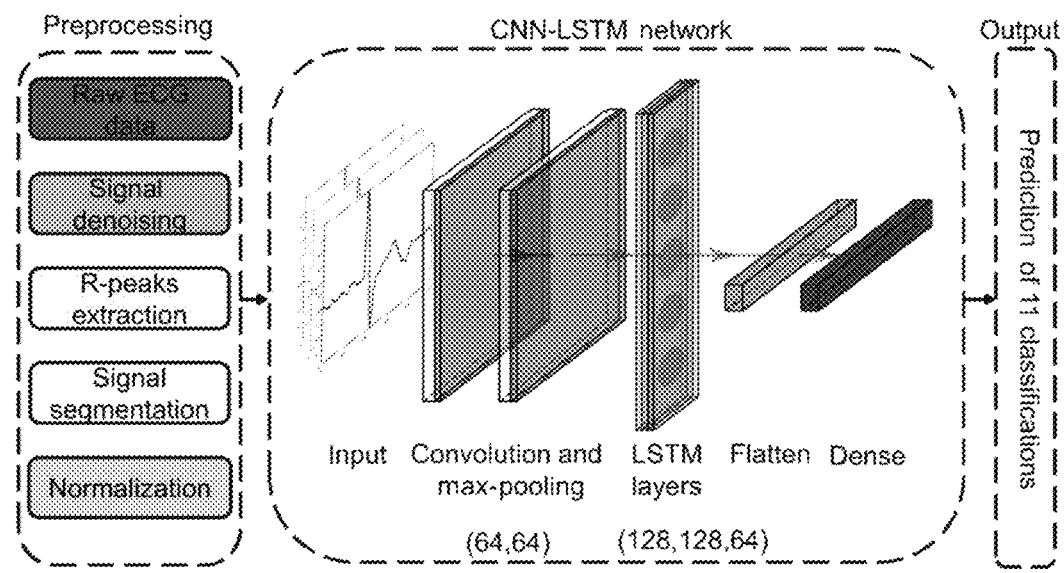
FIG. 5 depicts a block diagram illustrating an arrhythmia detection algorithm used by the 3-leads ECG system to predict heart rhythm.

In one embodiment, a more accurate prediction of heart rhythm abnormality and in turn probability of a CVD condition of the subject user is made using an arrhythmia detection algorithm executed by the electronic UI and/or one or more computer servers connected with the electronic UI. The arrhythmia detection algorithm comprises two main stages: a signal pre-processing and a machine learning (ML)-based heart rhythm classification. FIG. 5 shows a logical block diagram of the arrhythmia detection algorithm.

The waveform of ECG signal is a typically weak electrical signal in a millivolt scale. Because of the subject user's movements and electrical interference, the measured ECG signal typically contains various noises that reduce the accuracy of the heart rhythm classification. Therefore, before the heart rhythm classification, a pre-processing with a signal denoising step is performed on the measured ECG signal data (raw data). Wavelet transform is an effective technique for signal denoising. The signal denoising step comprises a 11-level decomposition on the measured ECG signal data using discrete wavelet transform (DWT) to remove high-frequency noise such as powerline interference and low-frequency noise such as baseline wandering, with Daubechies6 (DB6) wavelets. After artifacts deduction, main features such as the QRS complex remained in signal reconstruction. Then, a Pan-Tomkins algorithm is used to extract the R-peak locations to make a plurality of measured ECG signal data segments. In the signal segmentation, measured ECG signal data during the 0.4 second before and 0.5 second after the R-peak are selected as a heartbeat segment. The signal segmentation produces the main features of a heart rhythm, including QRS complex, P wave, and T wave. To reduce the misclassification caused by the imbalanced sample distribution, SMOTE is used for data augmentation, After resampling (i.e., 250 Hz) and normalization, the resulting preprocessed measured. ECG signal data of 11 classes are treated as the input to the heart rhythm classification model.

The heart rhythm classification model comprises two crucial modules: a convolutional neural network (CNN) and long short-term memory (LSTM) network. The CNN is a classical and widely used deep learning network that effectively reduces the complexity of the network and extracts features from complex data. In one embodiment, a one-dimensional (1D) CNN is employed due to the 1D time-series input. For the pooling layers, max-pooling 1D is used to calculate the maximum values of the field. The CNN module includes two CNN layers and two max-pooling layers, and the filters numbers are 64 with the same kernel size of 3×1 for each layer. After the pattern's extraction via the CNN module, the feature map serves as the input into the subsequent LSTM module. Due to the unique gate structure of the LSTM cell, the LSTM exhibits better performance in long-term series tasks than the traditional neural network. There are three LSTM layers connected to the CNN layers, and each hidden layer includes 128, 128, and 64 hidden neurons, respectively. In addition, a batch normalization layer is added behind each convolutional layer and LSTM layer to avert overfitting. Finally, the last parts of the network are a flatten layer and a fully connected layer with 11 neurons activated by the Softmax function. The classification outputs are 11 types of heart rhythm prediction probabilities, including NORMAL N Normal beat, PVC V Premature ventricular contraction, APC A Atrial premature beat, LBBB L Left bundle branch block beat, RBBB R Right bundle branch block beat. NPC J Nodal (junctional) premature beat, NESC j Nodal (junctional) escape beat; UNKNOWN Q Unclassifiable beat, SVPB S Supraventricular premature or ectopic beat (atrial or nodal), VESC F Ventricular escape beat, and PFUS f Fusion of paced and normal beat.

In one test, the heart rhythm classification model was trained at a learning rate of 0.001 and with a batch size of 64. The training process took 100 epochs.

The functional units of the apparatuses and the methods in accordance to embodiments disclosed herein may be implemented using computing devices, computer processors, or electronic circuitries including but not limited to application specific integrated circuits (ASIC), field programmable gate arrays (FPGA), and other programmable logic devices configured or programmed according to the teachings of the present disclosure. Computer instructions or software codes running in the computing devices, computer processors, or programmable logic devices can readily be prepared by practitioners skilled in the software or electronic art based on the teachings of the present disclosure.

All or portions of the methods in accordance to the embodiments may be executed in one or more computing devices including server computers, personal computers, laptop computers, mobile computing devices such as smartphones and tablet computers.

The embodiments include computer storage media having computer instructions or software codes stored therein which can be used to program computers or microprocessors to perform any of the processes of the present invention. The storage media can include, but are not limited to, floppy disks, optical discs. Blu-ray Disc, DVD, CD-ROMs, and magneto-optical disks, ROMs, RAMs, flash memory devices, or any type of media or devices suitable for storing instructions, codes, and/or data.

Each of the functional units in accordance to various embodiments also may be implemented in distributed computing environments and/or Cloud computing environments, wherein the whole or portions of machine instructions are executed in distributed fashion by one or more processing devices interconnected by a communication network, such as an intranet, Wide Area. Network (WAN), Local Area Network (LAN), the Internet, and other forms of data transmission medium.

The foregoing description of the present invention has been provided for the purposes of illustration and description. It is not intended to be exhaustive or to limit the invention to the precise forms disclosed. Many modifications and variations will be apparent to the practitioner skilled in the art.

While the present disclosure has been described and illustrated with reference to specific embodiments thereof, these descriptions and illustrations are not limiting. It should be understood by those skilled in the art that various changes may be made and equivalents may be substituted without departing from the true spirit and scope of the present disclosure as defined by the appended claims. The illustrations may not necessarily be drawn to scale. There may be distinctions between the artistic renditions in the present disclosure and the actual apparatus due to manufacturing processes and tolerances. There may be other embodiments of the present disclosure which are not specifically illustrated. The specification and the drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations.

What is claimed is:

1. A multi-leads electrocardiogram (ECG) monitoring apparatus, comprising:
   a stretchable and flexible main patch containing a primary circuitry, wherein the main patch is worn on a body of a subject user by adhesion on skin during use; and
   at least four flexible leads, each lead connecting to the primary circuitry at a first end and connecting to an ECG electrode patch at a second end, wherein each of the ECG electrode patches is worn on a skin area of the body of the subject user, which is not wearing another one of the ECG electrode patches, by adhesion on skin during use for measuring ECG signals;
   wherein the primary circuitry is configured to receive measured ECG signals from the ECG electrode patches via the leads, process the measured ECG signals received, generate and transmit measured ECG signal data to a computing device implementing an electronic user interface (UI) for displaying of the measured ECG signal data;
   wherein the ECG electrode patches are organohydrogel ECG electrode patches; and
   wherein organohydrogel material of the organohydrogel ECG electrode patches is fabricated by a photo-triggered gelation procedure in a binary solvent of glycerol-water for enhanced adhesion strength and enhanced sustained conductivity;
   wherein the computing device implementing the electronic UI is configured to execute an arrhythmia detection algorithm to predict heart rhythm abnormality from the measured ECG signal data;
   wherein the arrhythmia detection algorithm comprises:
      a signal pre-processing comprising signal denoising, data segmentation, data augmentation, data resampling, and normalization of the measured ECG signal data to generate preprocessed measured ECG signal data; and
   a machine learning (ML)-based heart rhythm classification configured to generate one or more types of heart rhythm prediction probabilities from the preprocessed measured ECG signal data; wherein the ML-based heart rhythm classification is implemented by a convolutional neural network (CNN) with a long short-term memory (LSTM) network.

2. The multi-leads ECG monitoring apparatus of claim 1, wherein the primary circuitry comprises a first electrode layer of soft printed circuit and a second electrode layer of soft printed circuit stacked on each other, forming a two-layer soft printed circuit;

wherein the first electrode layer includes electronic components and conductive traces, and the second electrode layer includes additional conductive traces, completing connections among the electronic components on the first electrode layer;

wherein layouts of the conductive traces are in interconnecting serpentine shape; and wherein the electronic components comprise at least:
 a microcontroller configured to process the measured ECG signal received from the leads, process control signals received from the electronic UI, and facilitate wireless data communication with the electronic UI and other external devices, and a wireless communication antenna.

3. The multi-leads ECG monitoring apparatus of claim 1, wherein the leads consist of three measurement leads for measuring ECG signals, and one neutral lead for applying a dynamic feedback signal to the body of the subject user;

wherein each of the ECG electrode patches connected to the leads is placed on one of human torsos of the subject user during use; and wherein the dynamic feedback signal is generated from a difference between an average of measured ECG signal voltage readings received from the three measurement leads and a reference voltage.

4. The multi-leads ECG monitoring apparatus of claim 1, wherein the photo-triggered gelation procedure comprises:
 adding a proportion equivalent to 1 g gelatin into a proportion equivalent to 9 ml deionized water;
 stirring the gelatin-deionized water mixture at 60° C. for 2 hours to produce a gelatin solution,
 adding a proportion equivalent to 2.1 g SBMA, a proportion equivalent to 0.9 g AAc, a proportion equivalent to 5 mg MBAA, a proportion equivalent to 50 mg 2959, a proportion equivalent to 0.33 g CaCl2, and a proportion equivalent to 3 ml glycerol into the gelatin solution to produce a mixed solution;
 degassing the mixed solution for 30 minutes; and
 placing the mixed solution at illumination of UV light for 30 minutes to produce an organohydrogel ionic polymer skeleton of the organohydrogel ECG electrode patches.

5. The multi-leads ECG monitoring apparatus of claim 1, wherein the primary circuitry further comprises:
 a plurality of instrumentation amplifiers with input of each of the instrumentation amplifiers connected to one or more of the leads and configured to receive measured ECG signals from the leads; and
 an operational amplifier for each of the instrumentation amplifiers with input of the operational amplifier connected to an output of the instrumentation amplifier;

wherein the instrumentation amplifiers and the operational amplifier are configured to amplify the measured ECG signals before further processing by the primary circuitry.

6. The multi-leads ECG monitoring apparatus of claim 1, wherein the main patch is primarily made of polydimethylsiloxane (PDMS).

7. The multi-leads ECG monitoring apparatus of claim 1, wherein each of the leads comprises wire is encapsulated in a layer of polydimethylsiloxane (PDMS).

8. The multi-leads ECG monitoring apparatus of claim 1, wherein the primary circuitry comprises a vibration actuator for tactile alarm configured to receive driving signals based on detections of abnormality in the measured ECG signals.

9. The multi-leads ECG monitoring apparatus of claim 1, wherein the types of heart rhythm prediction probabilities comprise: NORMAL N Normal beat, PVC V Premature ventricular contraction, APC A Atrial premature beat, LBBB L Left bundle branch block beat, RBBB R Right bundle branch block beat, NPC J Nodal (junctional) premature beat, NESC j Nodal (junctional) escape beat, UNKNOWN Q Unclassifiable beat, SVPB S Supraventricular premature or ectopic beat (atrial or nodal), VESC E Ventricular escape beat, and PFUS f Fusion of paced and normal beat.

10. A multi-leads electrocardiogram (ECG) monitoring apparatus, comprising:
 a stretchable and flexible main patch containing a primary circuitry, wherein the main patch is worn on a body of a subject user by adhesion on skin during use; and
 at least four flexible leads, each lead connecting to the primary circuitry at a first end and connecting to an ECG electrode patch at a second end, wherein each of the ECG electrode patches is worn on a skin area of the body of the subject user, which is not wearing another one of ECG electrode patches, by adhesion on skin during use for measuring ECG signals;

wherein the primary circuitry is configured to receive measured ECG signals from the ECG electrode patches via the leads, process the measured ECG signals received, generate and transmit measured ECG signal data to a computing device configured to execute an arrhythmia detection algorithm to predict heart rhythm abnormality from the measured ECG signal data;

wherein the arrhythmia detection algorithm comprises a machine learning (ML)-based heart rhythm classification configured to generate one or more types of heart rhythm prediction probabilities from a preprocessed measured ECG signal data generated from the measured ECG signal data; and wherein the ML-based heart rhythm classification is implemented by a convolutional neural network (CNN) with a long short-term memory (LSTM) network.

11. The multi-leads ECG monitoring apparatus of claim 10,
wherein the primary circuitry comprises a first electrode layer of soft printed circuit and a second electrode layer of soft printed circuit stacked on each other, forming a two-layer soft printed circuit;

wherein the first electrode layer includes electronic components and conductive traces, and the second electrode layer includes additional conductive traces, completing connections among the electronic components on the first electrode layer;

wherein layouts of the conductive traces are in interconnecting serpentine shape; and wherein the electronic components comprise at least:
 a microcontroller configured to process the measured ECG signal received from the leads, process control signals received from an electronic UI configured for displaying of the measured ECG signal data, and facilitate wireless data communication with the electronic UI and other external devices, and a wireless communication antenna.

12. The multi-leads ECG monitoring apparatus of claim 10,
   wherein the leads consist of three measurement leads for measuring ECG signals, and one neutral lead for applying a dynamic feedback signal to the body of the subject user;
   wherein each of the ECG electrode patches connected to the leads is placed on one of human torsos of the subject user during use; and
   wherein the dynamic feedback signal is generated from a difference between an average of measured ECG signal voltage readings received from the three measurement leads and a reference voltage.

13. The multi-leads ECG monitoring apparatus of claim 10,
   wherein the ECG electrode patches are organohydrogel ECG electrode patches; and
   wherein an organohydrogel material of the organohydrogel ECG electrode patches is fabricated by a photo-triggered gelation procedure in a binary solvent of glycerol-water.

14. The multi-leads ECG monitoring apparatus of claim 13,
   wherein the photo-triggered gelation procedure comprises:
      adding a proportion equivalent to 1 g gelatin into a proportion equivalent to 9 ml deionized water;
      stirring the gelatin-deionized water mixture at 60° C. for 2 hours to produce a gelatin solution;
      adding a proportion equivalent to 2.1 g SBMA, a proportion equivalent to 0.9 g AAc, a proportion equivalent to 5 mg MBAA, a proportion equivalent to 50 mg 2959, a proportion equivalent to 0.33 g $CaCl_2$, and a proportion equivalent to 3 ml glycerol into the gelatin solution to produce a mixed solution;
      degassing the mixed solution for 30 minutes; and
      placing the mixed solution at illumination of UV light for 30 minutes to produce an organohydrogel ionic polymer skeleton of the organohydrogel ECG electrode patches.

15. The multi-leads ECG monitoring apparatus of claim 10,
   wherein the primary circuitry further comprises:
      a plurality of instrumentation amplifiers with input of each of the instrumentation amplifiers connected to one or more of the leads and configured to receive measured ECG signals from the leads; and
      an operational amplifier for each of the instrumentation amplifiers with input of the operational amplifier connected to an output of the instrumentation amplifier;
   wherein the instrumentation amplifiers and the operational amplifier are configured to amplify the measured ECG signals before further processing by the primary circuitry.

16. The multi-leads ECG monitoring apparatus of claim 10,
   wherein the main patch is primarily made of polydimethylsiloxane (PDMS).

17. The multi-leads ECG monitoring apparatus of claim 10,
   wherein each of the leads comprises wire is encapsulated in a layer of polydimethylsiloxane (PDMS).

18. The multi-leads ECG monitoring apparatus of claim 10,
   wherein the primary circuitry comprises a vibration actuator for tactile alarm configured to receive driving signals based on detections of abnormality in the measured ECG signals.

* * * * *